(12) United States Patent
Steenhoek et al.

(10) Patent No.: US 10,928,327 B2
(45) Date of Patent: Feb. 23, 2021

(54) APPARATUSES AND METHODS FOR MEASURING SPATIAL PROPERTIES OF SURFACE COATING CONTAINING FLAKE PIGMENT

(71) Applicant: AXALTA COATING SYSTEMS IP CO., LLC, Wilmington, DE (US)

(72) Inventors: Larry E. Steenhoek, Wilmington, DE (US); Hardeep Singh Gill, Greenville, DE (US); Ken S. Schermacher, Chadds Ford, PA (US)

(73) Assignee: AXALTA COATING SYSTEMS IP CO., LLC, Wilmington, DE (US)

(*) Notice: Subject to any disclaimer, the term of this patent is extended or adjusted under 35 U.S.C. 154(b) by 191 days.

(21) Appl. No.: 15/838,137

(22) Filed: Dec. 11, 2017

(65) Prior Publication Data
US 2018/0180556 A1   Jun. 28, 2018

Related U.S. Application Data

(60) Provisional application No. 62/437,707, filed on Dec. 22, 2016.

(51) Int. Cl.
*G01N 21/84* (2006.01)
*G01N 21/55* (2014.01)
(Continued)

(52) U.S. Cl.
CPC ....... *G01N 21/8422* (2013.01); *G01B 11/303* (2013.01); *G01J 3/504* (2013.01);
(Continued)

(58) Field of Classification Search
CPC .... G01N 21/17; G01N 21/1717; G01N 21/25; G01N 21/253; G01N 21/255;
(Continued)

(56) References Cited

U.S. PATENT DOCUMENTS

| | | | | |
|---|---|---|---|---|
| 4,746,805 A | * | 5/1988 | Stapleton | G01N 21/57 250/559.16 |
| 5,078,496 A | * | 1/1992 | Parker | G01B 11/303 356/446 |

(Continued)

*Primary Examiner* — Gordon J Stock, Jr.
(74) *Attorney, Agent, or Firm* — Lorenz & Kopf, LLP

(57) ABSTRACT

Apparatuses and methods for measurement of spatial properties of a moving surface coating containing flake pigment are provided herein. An exemplary apparatus includes a movable surface adapted to receive the surface coating. A motion device is in mechanical communication with the movable surface. A light source provides a beam of light directed at a preselected interrogation zone through which the movable surface passes during movement thereof. A light detection device detects light reflected from the preselected interrogation zone and produces an output. A computing device is configured to determine one or more spatial properties of the surface coating based upon the output. One or more of the light source, the light detection device, or the computing device are configured to adjust for the movement of the surface coating through the preselected interrogation zone as a variable that affects measurement of reflected light by the light detection device.

20 Claims, 4 Drawing Sheets

(51) Int. Cl.
*G01N 33/32* (2006.01)
*G01J 3/50* (2006.01)
*G01N 1/28* (2006.01)
*G01B 11/30* (2006.01)
*G01N 21/57* (2006.01)
*G01N 21/47* (2006.01)

(52) U.S. Cl.
CPC ............ *G01N 1/2813* (2013.01); *G01N 21/55* (2013.01); *G01N 33/32* (2013.01); *G01N 21/57* (2013.01); *G01N 2021/4769* (2013.01); *G01N 2021/4771* (2013.01); *G01N 2021/8427* (2013.01)

(58) Field of Classification Search
CPC ...... G01N 21/256; G01N 21/27; G01N 21/29; G01N 21/293; G01N 21/47; G01N 21/4738; G01N 21/55; G01N 21/57; G01N 21/84; G01N 21/8422; G01N 2021/1734; G01N 2021/1736; G01N 2021/1765; G01N 2021/1768; G01N 2021/177; G01N 2021/1772; G01N 2021/1774; G01N 2021/1776; G01N 2021/1778; G01N 2021/178; G01N 2021/1782; G01N 2021/4735; G01N 2021/4764; G01N 2021/4771; G01N 2021/4783; G01N 2021/556; G01N 2021/557; G01N 2021/559; G01N 2021/575; G01N 2021/8405; G01N 2021/8416; G01N 2021/8427; G01N 2021/8433; G01N 2021/8438; G01N 33/32; G01N 1/2813; G01N 2021/4773; G01N 2021/4776; G01N 2021/4769; G01B 11/30; G01B 11/303; G01B 11/306; G01J 3/46; G01J 3/462; G01J 3/463; G01J 3/465; G01J 3/526; G01J 3/504
See application file for complete search history.

(56) References Cited

U.S. PATENT DOCUMENTS

| | | | | |
|---|---|---|---|---|
| 6,178,254 B1* | 1/2001 | Rappette | ............. | B41F 33/0045 250/559.01 |
| 6,721,054 B1* | 4/2004 | Spooner | ............... | G01N 21/274 250/339.07 |
| 6,760,475 B1* | 7/2004 | Miller | ........................ | G01J 3/26 348/E9.01 |
| 6,891,617 B2* | 5/2005 | Alman | ....................... | G01J 3/46 356/244 |
| 6,952,265 B2 | 10/2005 | Prakash et al. | | |
| 6,975,404 B2 | 12/2005 | Schwarz | | |
| 7,466,415 B2* | 12/2008 | Gibson | ............... | B01F 13/1055 356/402 |
| 10,386,235 B2* | 8/2019 | Ehbets | ............... | G01N 21/4785 |
| 2004/0252308 A1* | 12/2004 | Prakash | ............. | G01N 21/4738 356/445 |
| 2008/0013818 A1* | 1/2008 | Shakespeare | ........ | G01B 11/306 382/141 |
| 2008/0123106 A1* | 5/2008 | Zeng | .................... | A61B 5/0066 356/600 |
| 2009/0097033 A1* | 4/2009 | Kuusela | ............... | G01N 33/346 356/446 |
| 2013/0107266 A1* | 5/2013 | Moy | ...................... | G01N 21/55 356/445 |
| 2013/0141713 A1* | 6/2013 | Saliya | .................... | G01N 21/57 356/36 |
| 2013/0141724 A1* | 6/2013 | Yokoyama | ................. | G01J 3/50 356/402 |
| 2013/0141727 A1* | 6/2013 | Yokoyama | ............. | G01N 21/55 356/445 |
| 2014/0078293 A1* | 3/2014 | Beymore | ................ | G01J 3/504 348/135 |
| 2015/0160122 A1* | 6/2015 | Moy | ..................... | G01N 1/2813 73/150 R |
| 2015/0160123 A1* | 6/2015 | Moy | .................. | G01N 21/8422 356/402 |
| 2016/0069802 A1* | 3/2016 | Moy | ..................... | G01N 21/57 356/338 |

* cited by examiner

APPARATUSES AND METHODS FOR MEASURING SPATIAL PROPERTIES OF SURFACE COATING CONTAINING FLAKE PIGMENT

CROSS-REFERENCE TO RELATED APPLICATIONS

This application claims the benefit of U.S. Provisional Application No. 62/437,707 filed Dec. 22, 2016.

TECHNICAL FIELD

The technical field generally relates to apparatuses and methods for measurement of spatial properties of a surface coating, and more particularly relates to apparatuses and methods for measurement of spatial properties of a surface coating that contains flake pigment.

BACKGROUND

Surface coatings containing a flake pigment, for example metal flake pigments such as aluminum flake, are well known. The surface coatings containing the flake pigment are particularly favored for the protection and decoration of automobile bodies, such as for example by reason of their imparting a differential light reflection effect, usually referred to as "flop". The surface coatings containing the flake pigment also provide unique appearance effects, which include sparkle imparted by the flake as well as the enhancement of the perception of depth in the coating. In practice, a proportion of the flakes lie parallel in the surface coatings; the remainder lie at various angles to the surface plane, i.e. there is a distribution of the orientations of the flakes in the surface coating. The degree of sparkle in the surface coating is a function of the flake size, surface smoothness of the flakes, orientation of the flakes, and uniformity of the flake edges. Metallic coatings usually also contain pigments, generally of a light absorbing rather than a light scattering type. Any light scatter from the pigments or the flakes themselves, e.g., from the flake edges, diminishes the flop of the coating.

Instrumental characterization of surface coatings containing the flake pigment can, in principle, be carried out by measuring the spectral reflectance of a coated panel with a spectrophotometer. Measurements are generally made at a number of angles of incident illumination and of viewing, either within the plane of the illumination and viewing axes, or outside of this plane. The results of such measurements using the spectrophotometer are dependent on the degree of flake alignment as well as the type of flake or other pigments used, but give no direct evidence of spatial properties such as the degree of sparkle or flake size, which correlates to coarseness or graininess of the surface coating. As a result, the measurements from the spectrophotometer in characterizing the surface coating are insufficient to fully characterize these materials.

In color matching a previously coated substrate of an automotive body, it is necessary to choose both the correct pigments to match the color of that substrate as well as the correct flake to match the color and appearance of that substrate. For an effective measure of the flake characteristics such as size or degree of sparkle of the flakes to be obtained, therefore, it is necessary under these circumstances for formulators to select, based on their expertise, the flake pigment to be used by visually analyzing the target surface, such as a previously coated substrate of an automotive body. Once the flake pigment has been identified, the pigments are selected, typically by well-known computer based algorithms such as those based on radiative transfer theory, which mathematically adjust the pigment quantities, add or reduce black and white pigment quantities, and which also mathematically adjust flop adjuster quantities, including flake quantities, so that the error in the color and flop match to the target surface is the lowest while ensuring that the resulting color/flop formulation is still within the bounds of accepted commercial practice. This formulation is then made up and sprayed on test panels, which are then visually compared to the target surface. If the flop and/or sparkle match are deemed unsatisfactory, the formulator adjusts the type and/or changes the amount of the flake pigment entered into the algorithm to get new color/flop formulation and the whole cycle is repeated until an adequate match is achieved in both color and appearance at all relevant angles of illumination and view.

Existing devices are available for optically analyzing surface coatings for purposes of determining spatial properties such as sparkle, coarseness, and graininess. Such devices generally include a light source configured to illuminate the surface coating, an optical detector including a plurality of light-sensitive sensors for recording the light reflected from the surface coating, and a controller that is configured to process the output from the optical detector to determine sparkle, coarseness, or graininess of the surface coating. In particular, the devices are generally placed on a cured, immobile substrate having the surface coating with the light source and detector directed at a preselected interrogation zone of the surface coating. The light-sensitive sensors generally record intensity of the detected light, with the output from the plurality of light-sensitive sensors arranged into a pixelated optical image representative of a defined area of the surface coating. The controller integrates the detected intensities and intensity area derived from the pixelated optical image to render a sparkle determination. However, to effectively analyze the surface coatings, static measurement with the devices is required. More specifically, the devices are incapable of accurately optically analyzing surface coatings that are in motion, due to the impact of movement on the intensities detected by the plurality of light-sensitive sensors. In effect, motion of the surface coating results in blurriness of the pixelated optical image provided by the optical detector, thereby negatively affecting accurate determination of intensity and intensity area correlating to the flake pigments. It is time consuming to optically analyze immobile substrates, and it is even more time consuming to cure the surface coating prior to optically analyzing.

Accordingly, it is desirable to provide apparatuses and methods for measuring spatial properties of surface coatings that contain flake pigment that enable accurate determination of the spatial properties even when the surface coatings are in motion. Furthermore, other desirable features and characteristics will become apparent from the subsequent detailed description and the appended claims, taken in conjunction with the accompanying drawings and this background.

BRIEF SUMMARY

Apparatuses and methods for measurement of spatial properties of a moving surface coating containing flake pigment are provided herein. In an embodiment, an apparatus for measurement of spatial properties of a moving surface coating containing flake pigment includes a movable surface that is adapted to receive the surface coating. A motion device is in mechanical communication with the movable surface for moving the movable surface. A light source is positioned to provide a beam of light directed at a preselected interrogation zone through which at least a portion of the movable surface passes during movement thereof. A light detection device is positioned to detect light reflected from the preselected interrogation zone through which at least the portion of the movable surface passes during movement thereof. The light detection device produces an output that includes data representative of a detected intensity of scattered light and area of scattered light reflected by individual flake pigments in portions of the surface coating within the preselected interrogation zone. A computing device is coupled to the light detection device, optionally the light source, and optionally the motion device. The computing device is configured to determine one or more spatial properties of the surface coating based upon the output from the light detection device. One or more of the light source, the light detection device, or the computing device are configured to adjust for the movement of the surface coating through the preselected interrogation zone as a variable that affects measurement of reflected light from the preselected interrogation zone by the light detection device.

In another embodiment, a method of measuring spatial properties of a moving surface coating containing flake pigment includes moving a movable surface having the surface coating disposed thereon. A beam of light is directed at a preselected interrogation zone through which at least a portion of the movable surface passes during movement thereof. Reflected light is detected from the preselected interrogation zone through which at least the portion of the movable surface passes during movement thereof using a light detection device to produce an output that includes data representative of a detected intensity of reflected light and area of reflected light from individual flake pigments in portions of the surface coating within the preselected interrogation zone. One or more spatial properties of the surface coating is determined based upon the output from the light detection device using a computing device. The movement of the surface coating through the preselected interrogation zone is adjusted as a variable affecting detection of reflected light from the preselected interrogation zone by the light detection device.

In another embodiment, a method of measuring spatial properties of a moving surface coating containing flake pigment includes providing a wet surface coating on a substrate. The wet surface coating is adapted to move through a preselected interrogation zone. A beam of light is directed at the preselected interrogation zone through which at least a portion of the wet surface coating passes during movement thereof. Light that is reflected from the preselected interrogation zone through which at least the portion of the wet surface coating passes during movement thereof is detected using a light detection device to produce an output that includes data representative of a detected intensity of reflected light and area of reflected light from individual flake pigments in portions of the surface coating within the preselected interrogation zone. One or more spatial properties of the wet surface coating is determined based upon the output from the light detection device using a computing device. The movement of the wet surface coating through the preselected interrogation zone is adjusted as a variable affecting detection of reflected light from the preselected interrogation zone by the light detection device.

BRIEF DESCRIPTION OF THE DRAWINGS

The various embodiments will hereinafter be described in conjunction with the following drawing figures, wherein like numerals denote like elements, and wherein.

DETAILED DESCRIPTION

Figure 1:
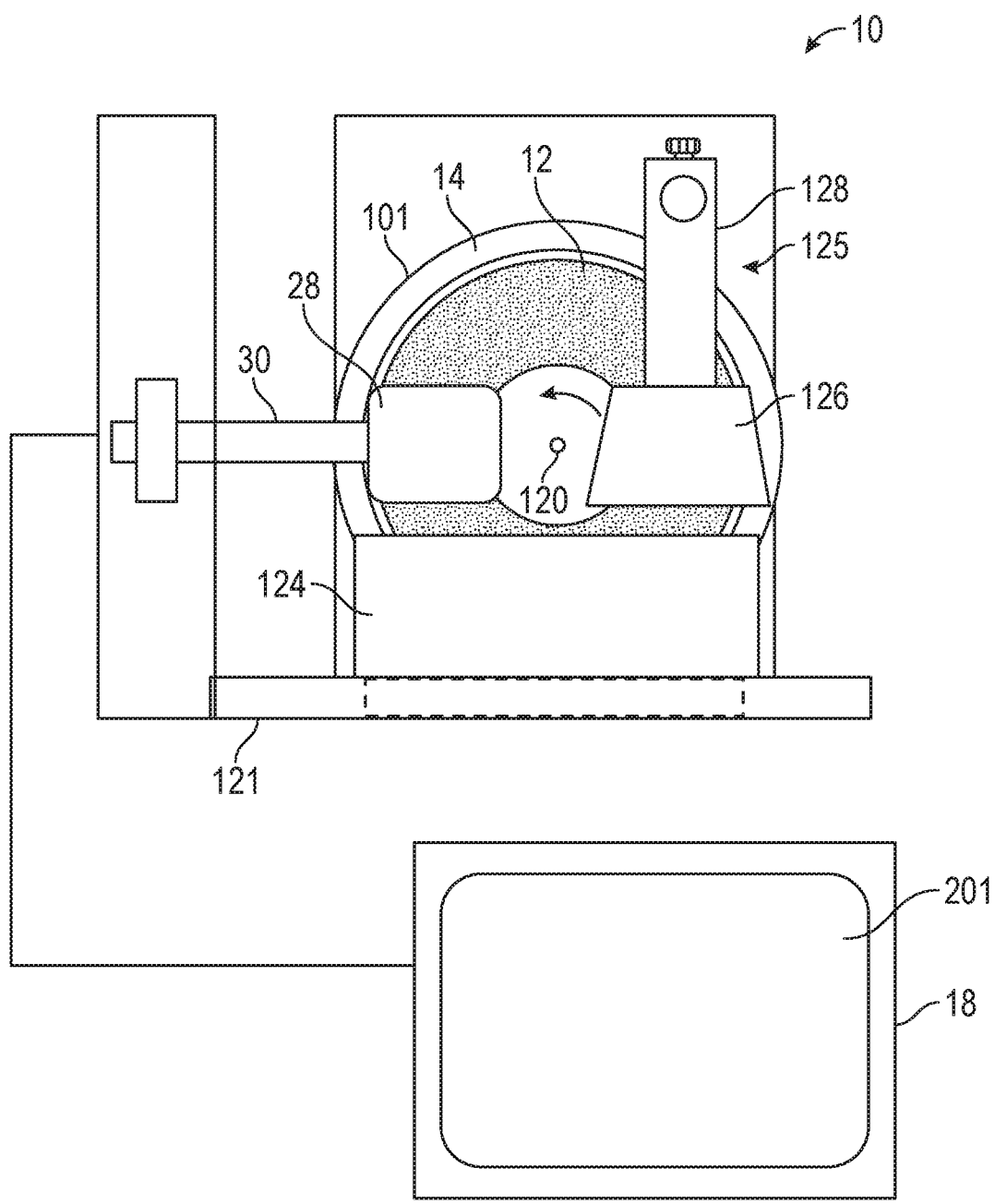
FIG. 1 is a front view of an apparatus for measuring spatial properties of a moving surface coating in accordance with an embodiment.

The following detailed description is merely exemplary in nature and is not intended to limit the apparatuses and methods for measuring spatial properties of a moving surface coating containing flake pigment. Furthermore, there is no intention to be bound by any theory presented in the preceding background or the following detailed description. The features and advantages of the various embodiments will be more readily understood, by those of ordinary skill in the art, from reading the following detailed description. It is to be appreciated that certain features of the subject matter disclosed herein, which are, for clarity, described above and below in the context of separate embodiments, may also be provided in combination in a single embodiment. Conversely, various features of the subject matter disclosed herein that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

A computing device used herein can refer to a data processing chip, a desktop computer, a laptop computer, a pocket PC, a personal digital assistant (PDA), a handheld electronic processing device, a smart phone that combines the functionality of a PDA and a mobile phone, or any other electronic devices that can process information automatically. A computing device can be built into other electronic devices, such as a built-in data processing chip integrated into an imaging device, color measuring device, or an appearance measuring device. A computing device can have one or more wired or wireless connections to a database, to another computing device, or a combination thereof. A computing device can be a client computer that communicates with a host computer in a multi-computer client-host system connected via a wired or wireless network including intranet and internet. A computing device can also be configured to be coupled with a data input or output device via wired or wireless connections. For example, a laptop computer can have data input devices such as key board, USB connections, or a touch screen and can be operatively configured to receive data and images through wired or wireless connections. A "portable computing device" can include a laptop computer, a pocket PC, a personal digital assistant (PDA), a handheld electronic processing device, a mobile phone, a smart phone, a tablet computer, or any other electronic devices that can process information and data and can be carried by a person.

Wired connections can include hardware couplings, splitters, adaptors, connectors, cables or wires. Wireless connections and devices can include, but are not limited to, Wi-Fi devices, Bluetooth devices, wide area network (WAN) wireless devices, local area network (LAN) devices, infrared communication devices, optical data transfer devices, radio transmitter and optionally receivers, wireless phones, wireless phone adaptor cards, or any other devices that can transmit signals in a wide range of radio frequency including visible or invisible optical wavelengths and electromagnetic wavelengths.

The term "wet" refers to a state of being liquid that is able to flow or adapt into a shape, such as the shape of a container or a substrate. Examples of wet compositions can include wet inks that have not dried or cured or wet coating compositions that have not dried or cured. A wet coating composition can be in a storage container or over a coated substrate and can adapt to the shape of the container or the shape of the substrate. A wet coating composition can comprise one or more liquid solvents, such as water, one or more organic solvents, one or more inorganic solvents, or a combination thereof. The "wet" property values refer to the property associated with composition values when the composition is wet. A wet coating composition refers to a film or surface of the coating composition that is wet and not dry to the touch as determined by ASTM D1640.

"Spatial properties" used herein refer to properties based on direct measurements of light reflected from the flakes based on geometry, orientation, and/or composition of the flakes themselves at a given illumination angle. Specifically, spatial properties include, but are not limited to, sparkle and coarseness or graininess of the surface coating. In this regard, "spatial properties" can be directly related to characteristics of the flake pigments, e.g., the size, amount, surface flatness, and type of flake pigments that are incorporated in the coating composition to provide the desired sparkle, coarseness, or graininess to the surface coating produced therefrom. Spatial properties do not include properties of the surface coating that are an indirect result of the presence of the flakes (e.g., flop, which is a differential light reflecting effect that is only based in part on reflected light from flakes). The spatial properties can and generally do vary with varying viewing angles or varying illumination angles.

"Flake pigment" used herein includes any pigment in platelet form, i.e., generally having a length and a width that are significantly greater than thickness. Examples of flake pigments that may be used include metallic flakes, for example aluminum flakes; special effect pigments such as coated mica flakes and coated aluminum flakes; pearlescent flakes; or a combination thereof.

"Movable surface" used herein is any surface that is controllable within an apparatus to selectively move during measurement of spatial properties of a surface coating on the movable surface. The movable surface may be the surface of a rotatable disk within a thin film apparatus that is adapted to measure properties of a wet surface coating. Alternatively, the movable surface may be the surface of a cylindrical drum, a panel, or any article that is adapted to move under control by the apparatus during measurement of the spatial properties of the surface coating, with the surface coating being wet or dry.

"Preset" used herein means that the relevant parameter is a characteristic of the particular device and is generally not modified or not modifiable. "Predetermined" used herein means that that parameter can be controlled and modified in the particular device at issue.

Apparatuses and methods for measurement of spatial properties of a moving surface coating that contains flake pigment are provided herein. The apparatuses and methods enable accurate determination of the spatial properties, even when the surface coatings are in motion, by adjusting for the movement of the surface coating through a preselected interrogation zone as a variable that affects measurement of reflected light from the preselected interrogation zone by a light detection device. "Adjustment for the movement of the surface coating," as referred to herein, means that movement of the surface coating is attenuated or normalized as a variable that affects detection of the reflected light with the light detection device beyond the capabilities of the light detection device when employed in a conventional manner (e.g., beyond simply capturing an image of the surface coating with a camera), or that methodology for measurement of reflected light is employed that can be readily processed to exclude readings that are attributable to movement of the surface coating. Whereas conventional devices for optically analyzing surface coatings exhibit blurriness of pixelated optical images provided by the optical detector due to movement of the surface coating, movement of the surface coating may be effectively marginalized with the apparatuses and methods described herein through various techniques. For example, in an embodiment, a light source has an intensity based on a preset sensitivity of an imaging device and is modulated at a predetermined illumination duration based on movement speed of the surface coating, thereby only illuminating the surface coating long enough to effectively capture a snapshot of the surface coating using the imaging device but also illuminating the surface coating at sufficient intensity to enable saturation of the optical image captured by the imaging device despite the short duration of illumination. In other embodiments, an electrical current may be produced from detected light that is reflected from a preselected interrogation zone using, e.g., a photo diode, with a correlation applied by a computing device between duration of reflected light that produces the electrical current and a dimension of a flake pigment that provides the reflected light at a preset movement speed of the moving surface coating to thereby adjust for movement of the surface coating through the preselected interrogation zone as a variable affecting detection of reflected light. Additional details regarding the various embodiments are described in further detail below.

An embodiment of an apparatus 10 for measurement of spatial properties of a moving surface coating 12 containing flake pigment will now be described with reference to FIGS. 1-3. In this embodiment, the apparatus 10 includes a movable surface 14 that is adapted to receive the surface coating 12. In embodiments, the movable surface 14 is the surface of a rotatable disk 101. In particular, the rotatable disk 101 may be a circular, planar disk that includes the movable surface 14 as a first disk surface 14 and that further includes a second disk surface 15 on the opposite sides of the circular planar disk 101 from the first disk surface 14. However, it is to be appreciated that the movable surface 14 is not limited to a surface of a circular planar disk 101.

A motion device 16 is in mechanical communication with the movable surface 14 for moving the movable surface 14. In this embodiment, the rotatable disk 101 may be coupled to a rotation shaft 120 that is aligned with a rotational axis 110 of the rotatable disk 101, perpendicular to the disk surfaces 14, 15 for providing rotation to the rotatable disk 101 along the rotational axis 110. The motion device 16 may be coupled to the rotation shaft 120 for providing rotation to the rotation shaft 120. The apparatus 10 may further include a device frame 121 that positions the rotation shaft 120 and the rotatable disk 101. In embodiments, a motion control device 131 may be provided for controlling rotation speed, rotation direction, or a combination thereof, of the motion device 16. However, it is to be appreciated that in other embodiments, the motion control device 131 may be omitted and the motion device 16 may be controlled with a computing device 18 that controls other features in the apparatus 10.

In embodiments, a thickness control device 125 that includes a thin film setting edge 126 may be coupled to a frame connector 128 that couples the thin film setting edge 126 to the device frame 121. The frame connector 128 is movable with respect to the device frame 121 to adjust a distance 127 between the thin film setting edge 126 and the movable surface 14. The thickness control device 125 is positioned adjacent to the movable surface 14 of the rotatable disk 101, with the thin film setting edge 126 disposed substantially parallel to the movable surface 14. In embodiments, the thin film setting edge 126 overlaps with the rotatable disk 101 covering in a range of from about 50% to about 99% of the radius of the rotatable disk 101. In embodiments, a distance 127 between the thin film setting edge 126 and the movable surface 14 is in a range of from about 0.05 mm to about 5 mm and is adjustable via the frame connector 128.

The apparatus 10 may further include a first reservoir 124 for storing a coating composition that is employed to form the surface coating 12. The first reservoir 124 can be configured so that the coating composition, when present in the first reservoir 124, is in contact with at least a portion of the rotatable surface 14. The first reservoir 124 can be a dip reservoir, such as the one shown in FIG. 1A, or a cup reservoir (not shown). The dip reservoir 124 can have a portion of the rotatable disk 101 dipped within so the coating composition, when present, can be in contact with the rotatable surface 14 and the second surface 15 in the first reservoir 124. The cup reservoir can provide the coating composition to be in contact with only one of the surfaces, such as the rotatable surface 14 only.

The rotatable disk 101 can be so positioned that the coating composition, when present in the first reservoir 124, is moved by the rotatable disk 101, when in rotation, from the first reservoir 124 to the thin film setting edge 126 against gravity. The rotatable surface 14 can be made of stainless steel, polymers, plastics, glass, or a combination thereof. The rotatable surface 14 should be suitable for forming a thin film of the coating composition as the surface coating 12 thereon having substantially even thickness for at least a portion of the rotatable surface 14 large enough for measuring spatial properties of the moving surface coating 12.

Figure 3:
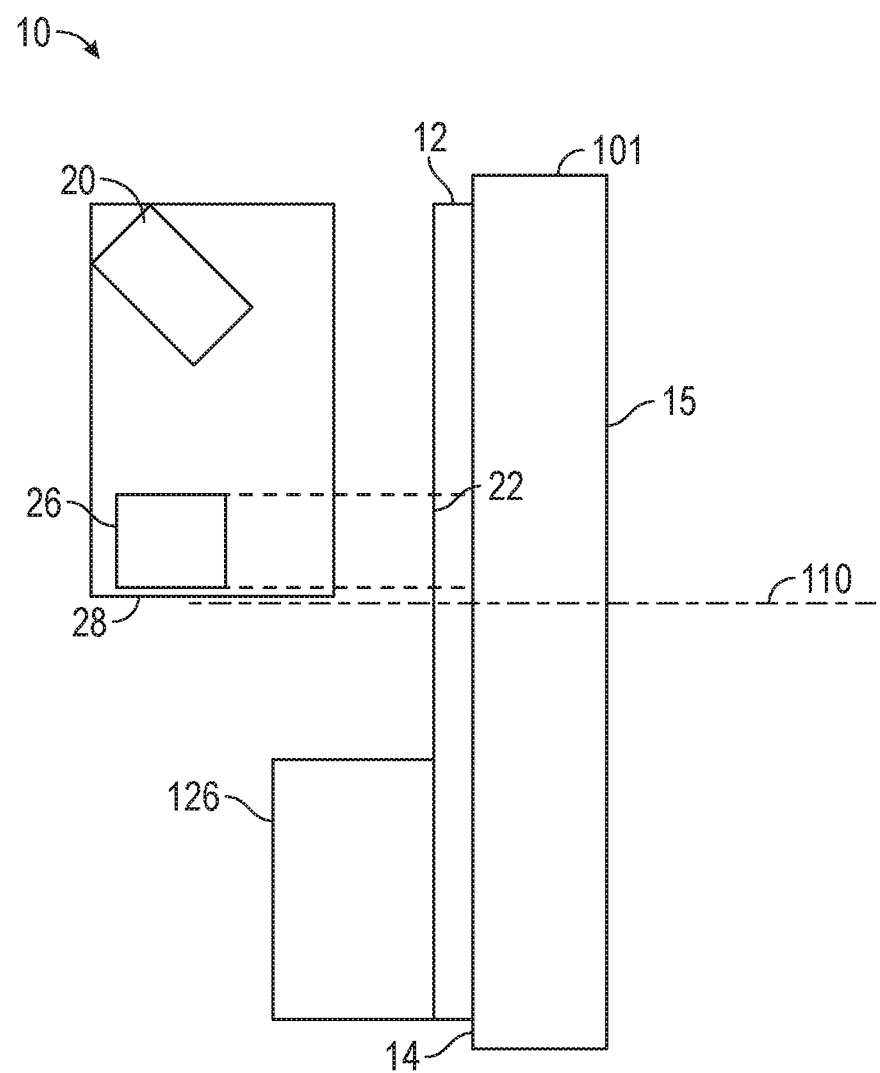
FIG. 3 is a schematic top view of the apparatus of FIG. 1.

Referring specifically to FIG. 3, the apparatus 10 further includes a light source 20 that is positioned to provide a beam of light directed at a preselected interrogation zone 22 through which at least a portion of the movable surface 14 passes during movement thereof. Multiple light sources 20 may be provided to provide light at multiple pre-set illumination angles, thereby enabling detection of reflection or spectrum at multiple pre-set illumination angles such as at 15°, 25°, 45°, and/or 75° from a plane normal to the movable surface 14. Alternatively, a single adjustable light source 20 can be employed, with the adjustable light source 20 being movable to provide illumination at all relevant angles. Furthermore, it is to be appreciated that the light source 20 may be included in a movable analytical device 28, as shown in FIGS. 1 and 3, with the analytical device 28 mounted to the device frame 121 through an movable mounting arm 30. In this regard, the preselected interrogation zone 22 may be a dynamic zone that changes based upon positioning of the movable analytical device 28. The light source 20 may be a high intensity light source such as a pulsed LED or laser.

As also shown in FIG. 3, the apparatus 10 further includes a light detection device 26 that is positioned to detect light reflected from the preselected interrogation zone 22 through which at least the portion of the movable surface 14 passes during movement thereof. The light detection device 26 may also be included in the movable analytical device 28, and the light detection device 26 may be positioned at a viewing angle that is on even plane with a plane normal to the movable surface 14 (i.e., the light detection device 26 may be positioned with a 90° viewing angle to the movable surface 14). The light detection device 26 produces an output that includes data representative of, but not limited to, a detected intensity of scattered light and area of scattered light reflected by individual flake pigments in portions of the surface coating 12 within the preselected interrogation zone 22. For example, in embodiments, the light detection device 26 is an imaging device and the output produced by the light detection device 26 is an optical image. The imaging device 26, which may be a video or a digital camera, includes a photosensitive surface for capturing the optical image of the preselected interrogation zone 22. The photosensitive surface can be a charged couple device sensor of a camera that produces the target image. The imaging device 26 may produce images in gray scale, in color or in both, such that the optical image is captured either as a gray target image or as a color image. One example of a suitable imaging device is a Pulnix® 7EX video camera supplied by Pulnix Inc., Sunnyvale, Calif. that produces gray scale images. Typically, a footprint of the gray or color optical images capable of being produced by imaging device 26 range from about 0.01 millimeters square to about 25.0 millimeters square, such as from about 0.25 millimeters square to 4 millimeters square, such as from about 0.5 millimeters square to 2.0 millimeters square. In embodiments, the footprint is a 1.5 millimeters square. Typically, imaging device 26 is capable of digitizing the gray or color optical image of the preselected interrogation zone 22 in the range of from 40,000 pixels to 16,000,000 pixels (640×480), wherein each pixel is capable of recognizing light intensities ranging from 16 to 65,536 levels for each of three primary color channels when the target image is in color. In embodiments, the imaging device 26 has a quantum efficiency of at least 40% at the wavelength of the light source 20.

In other embodiments, the light detection device 26 includes a photo diode that is configured to detect light reflected from the preselected interrogation zone 22. The photo diode 26 is configured to convert the detected light into an electrical current in accordance with conventional operation of photo diodes. It is to be appreciated that a plurality of photo diodes may be employed to detect light in various non-overlapping regions of the preselected interrogation zone 22. It is to also be appreciated that other measuring devices (not shown) beyond the imaging device 26 and that are determined suitable or developed by those skilled in the art for measuring the surface coating 12 can also be employed in the apparatus 10, and such other measuring devices may be included in the movable analytical device 28 or may be separate therefrom. For example, other measuring devices may include, but are not limited to, color measuring devices such as a colorimeter, a spectrophotometer, a goniospectrophotometer, or a combination thereof; a hiding measuring device a film thickness measuring device; or a combination thereof.

Figure 2:
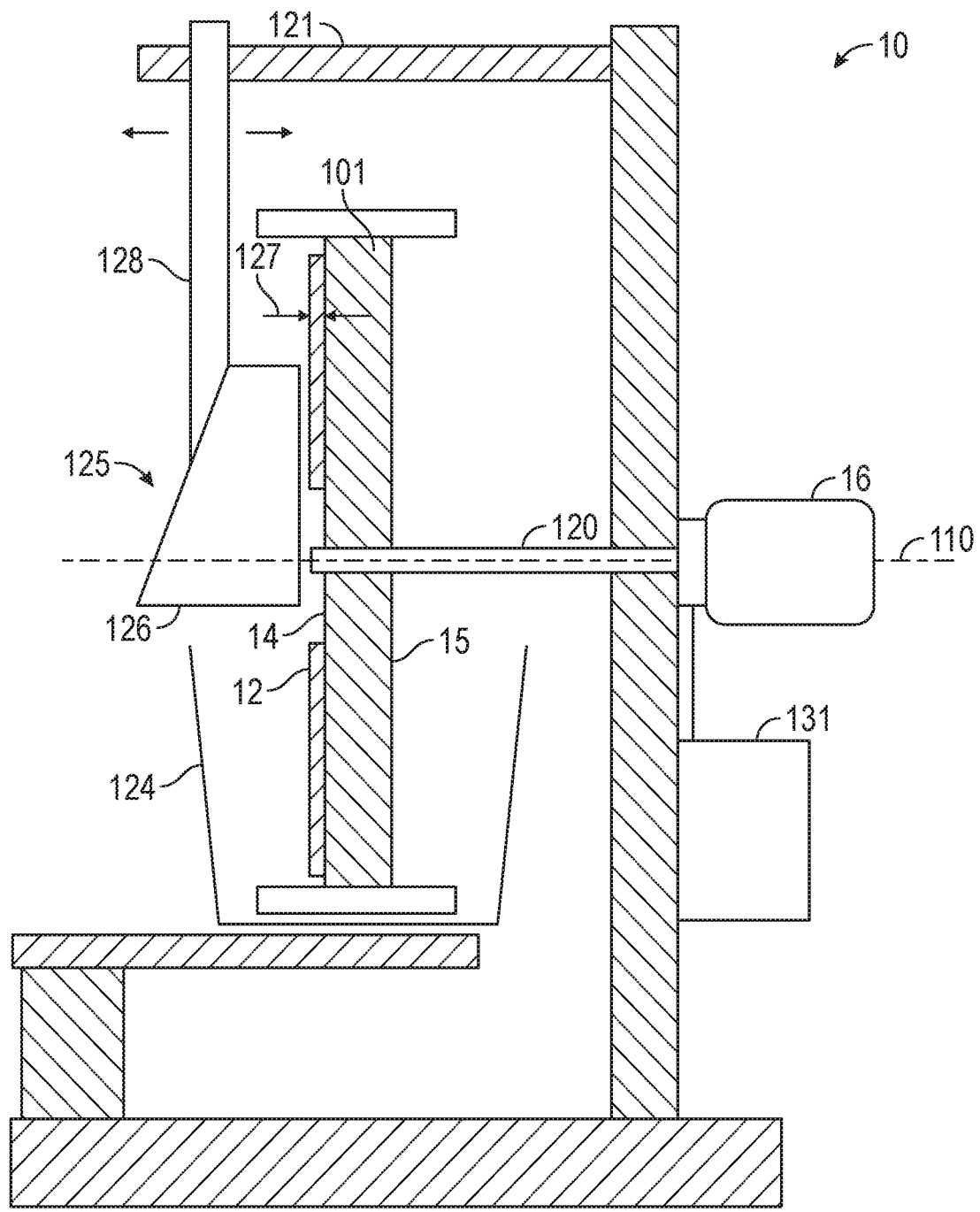
FIG. 2 is a cross-sectional side view of the apparatus of FIG. 1.

Referring to FIG. 1 and as alluded to above, the computing device 18 is coupled to the light detection device 26, optionally the light source 20, and optionally the motion device 16. The computing device 18 can also be coupled to any other measuring devices that may be present in the apparatus 10, as mentioned above. The computing device 18 can include a display device 201. Typical display devices, such a monitor, a TV, a high definition monitor, a touch screen, a HDR (high dynamic range) display, an LCD display screen, a plasma display screen, an LED display screen, a projector, a printer, or a combination thereof, are suitable. The computing device 18 can include one or more display devices. The computing device 18 and the display device 201 can be a single device, such as a laptop computer or tablet computer, separate devices coupled via wired or wireless connections, such as a laptop with a wired or wireless display connections for example Push2TV™ from NETGEAR® under trademark or registered trademark from NETGEAR Inc., San Jose, Calif. 95134-1911, or a combination thereof.

The computing device 18 is configured to determine one or more spatial properties of the surface coating 12 based upon the output from the light detection device 26. For example, a computing program product can be functionally coupled to the computing device 18 with the computing program product executed by the computing device 18 for rendering the aforementioned determinations.

In accordance with the various embodiments described herein, one or more of the light source 20, the light detection device 26, or the computing device 18 are configured to adjust for the movement of the surface coating 12 through the preselected interrogation zone 22 as a variable affecting measurement of reflected light from the preselected interrogation zone 22 by the light detection device 26. For example, in an embodiment in which the light detection device 26 is the imaging device, the imaging device 26 has a preset sensitivity, quantified by quantum efficiency of the imaging device 26, and the output produced by the light detection device 26 is the optical image. In this embodiment, the light source 20 and, optionally, the computing device 18 are configured to provide selective modulation of light from the light source 20 at an intensity that is based on the preset sensitivity of the imaging device 26 with modulation conducted at a predetermined illumination duration that is based on movement speed of the surface coating 12 and, optionally, size of the flake pigments to be measured so as to minimize blurriness of the resulting optical image. More specifically, in this embodiment, the computing device 18 may be in electronic communication with the light source 20 for controlling modulation of light from the light source 20. Alternatively, the light source 20 may be independent of the computing device 18 with modulation of light from the light source 20 controlled by the light source 20 itself. More particularly, the light source 20 may be a stand-alone device independent of an electronic connection with the computing device 18. In embodiments, the light source 20 is modulated to provide illumination for periods of from about 5 ns to about 5 μs with the surface coating 12 moving less than or equal to about 1.5 microns during illumination, such as less than or equal to about 0.003 microns during illumination. In embodiments, the light source 20 is chosen based on the quantum efficiency of the imaging device 26 to enable saturation of the optical image given a relatively short duration of illumination. For example, for illumination periods of from about 5 ns to about 5 μs and a quantum efficiency of the imaging device 26 of about 40%, the light source 20 may deliver about 1 mj/cm² to the measurement area over the illumination period. It is to be appreciated that in other embodiments in which there is no modulation of the light from the light source 20, conventional light sources may be employed that have a lesser intensity than the light source 20 of this embodiment.

To measure the spatial properties of the moving surface coating 12 in accordance with this embodiment, the surface coating 12 is applied wet onto the movable surface 14. In embodiments, measurement of the spatial properties of the surface coating 12 are conducted while the surface coating 12 is still wet, thereby providing for expediency and efficiency in measuring of the spatial properties. However, in embodiments, the surface coating 12 may be cured prior to measurement of the spatial properties thereof. The movable surface 14 having the surface coating 12 disposed thereon may then be moved, e.g., by rotating the movable surface 14 about the axis 110 using the motion device 16. Light is directed from the light source 20 at the preselected interrogation zone 22 through which at least a portion of the movable surface 14 passes during movement thereof, with the light modulated at the predetermined illumination duration. Light that is reflected from the preselected interrogation zone 22 is detected using the imaging device 26 to produce an optical image that includes data representative of, but not limited to, the detected intensity of reflected light and area of reflected light from individual flake pigments in portions of the surface coating 12 within the preselected interrogation zone 22. With the preset illumination duration based on movement speed of the surface coating 12, blurring of the resulting optical image may be diminished or eliminated by only providing illumination for the moment in time in which the imaging device 26 actively captures the optical image. In this manner, it is possible to adjust for the movement of the surface coating 12 through the preselected interrogation zone 22 as a variable affecting detection of reflected light from the preselected interrogation zone 22 by the light detection device 26.

One or more spatial properties of the surface coating 12 are determined based upon the output from the light detection device 26, more particularly the optical image, using the computing device 18. For example, in an embodiment, sparkle of the surface coating 12 is the spatial property that is determined. Various conventional techniques for determining sparkle from an optical image are known. For example, in this embodiment in which the light detection device 26 is the imagining device, the computing device 18 may be configured to determine sparkle of the surface coating 12 as the spatial property by integrating intensity and intensity area in the optical image for at least one range of intensities and at at least one angle of illumination. In particular, sparkle can be a function of sparkle intensity and sparkle area such as the function defined below:

$$S_G = f(S_i, S_a)$$

wherein, $S_G$, $S_i$ and $S_a$ are sparkle value, sparkling intensity, and sparkling area, respectively. One or more algorithms can be employed to define the function to calculate the $S_G$ from $S_i$ and $S_a$. The measured sparkle values can be obtained at one or more illumination angles, one or more viewing angles, or a combination thereof. The measured sparkle values can be obtained at one or more illumination angles. In one example, measured sparkle values can be obtained at 15° illumination angle. In another example, measured sparkle values can be obtained at 45° illumination angle. In yet another example, measured sparkle values can be obtained at 75° illumination angle. In a further example, measured sparkle values can be obtained at a combination of one or more of 15°, 25°, 45°, and 75° illumination angles. In embodiments, the measured sparkle values are obtained at a 0° viewing angle in relation to the plane normal to the movable surface 14. In other embodiments, the measured sparkle values can be obtained at one or more viewing angles, in relation to the plane normal to the movable surface 14, chosen from 0°, 15°, 25°, 45°, 75°, or a combination thereof. In embodiments, sparkle is determined based upon a thresholded optical image, where pixels having intensities below a threshold intensity are ignored and only pixels having an intensity at or above a certain, pre-selected threshold intensity are considered for purposes of the calculation. Specific methodologies for measuring characteristics of unknown flakes in a surface coating are described in U.S. Pat. No. 6,952,265, which is incorporated herein in its entirety.

As another example, the computing device 18 may be configured to determine coarseness of the surface coating 12 as the spatial property based on particle dimensions in the optical image, e.g., based on the largest identified particle dimension of each flake pigment in the optical image. Conventional algorithms may be employed to determine coarseness based upon coefficient of variation of the image as a measure of coarseness. To determine coefficient of variation, intensity of the entire image is assessed and, from the assessed intensity, a standard deviation is generated. The standard deviation is divided by the mean intensity to yield the coefficient of variation of the image.

In other embodiments in which the light detection device 26 includes the photo diode, the computing device 18 may be configured to determine sparkle of the surface coating 12 as the "spatial property" based upon frequency, intensity, and the duration of reflected light from the flake pigments as detected by the photo diode 26. The photo diode 26 picks up the reflected light and produces a corresponding analog electrical signal, which is then processed to determine the relative degree of intensity and intensity area. The electrical current produced by the photo diode(s) 26 may be processed based upon correlation between duration of reflected light detected from the photo diode 26 and a dimension of a flake pigment that provides the reflected light at a preset movement speed of the movable surface 14 to thereby indicate sparkle area, with the computing device 18 configured to apply the correlation. The electrical current produced by the photo diode(s) 26 may be further processed based upon a correlation between intensity of the detected reflected light attributable to a flake pigment and the resulting electrical current produced by the photo diode(s) 26 to thereby indicate sparkle intensity, with the computing device 18 configured to apply the correlation. Based upon such correlations, sparkle can be determined as a function of sparkle intensity and sparkle area in a similar manner as described above in the context of analysis of the optical image. More specifically, whereas determination of sparkle from an optical image may be based upon intensity of individual pixels in an array of pixels within the optical image, the electrical current produced by each photo diode 26 may be comparable to information obtained from a single row of pixels in the optical image. Thus, an array of photo diodes may be employed to produce a similar data set that can be obtained from an optical image. However, whereas determination of sparkle using the imaging device endeavors to effectively capture a snapshot of the preselected interrogation zone 22 and integrate intensity and intensity area based on the pixels in the optical image, the photo diode conversely relies upon movement of the movable surface 14 to provide frequency values for light reflected from the flake pigments and to thereby provide a data set of intensity and intensity area for integration.

In another embodiment, a wet surface coating is provided on a substrate. In this embodiment, the wet surface coating is adapted to move through a preselected interrogation zone, which may be defined as set forth above. In this embodiment, the substrate need not necessarily be movable, provided that the wet surface coating is still capable of moving through the preselected interrogation zone. For example, the substrate may be disposed with the wet surface coating deposited on a vertically-situated surface thereof such that the wet surface coating moves under the influence of gravity through the preselected interrogation zone. Measurement of the spatial properties of the wet surface coating may be conducted in the same manner as described above for all other embodiments.

Figure 4:
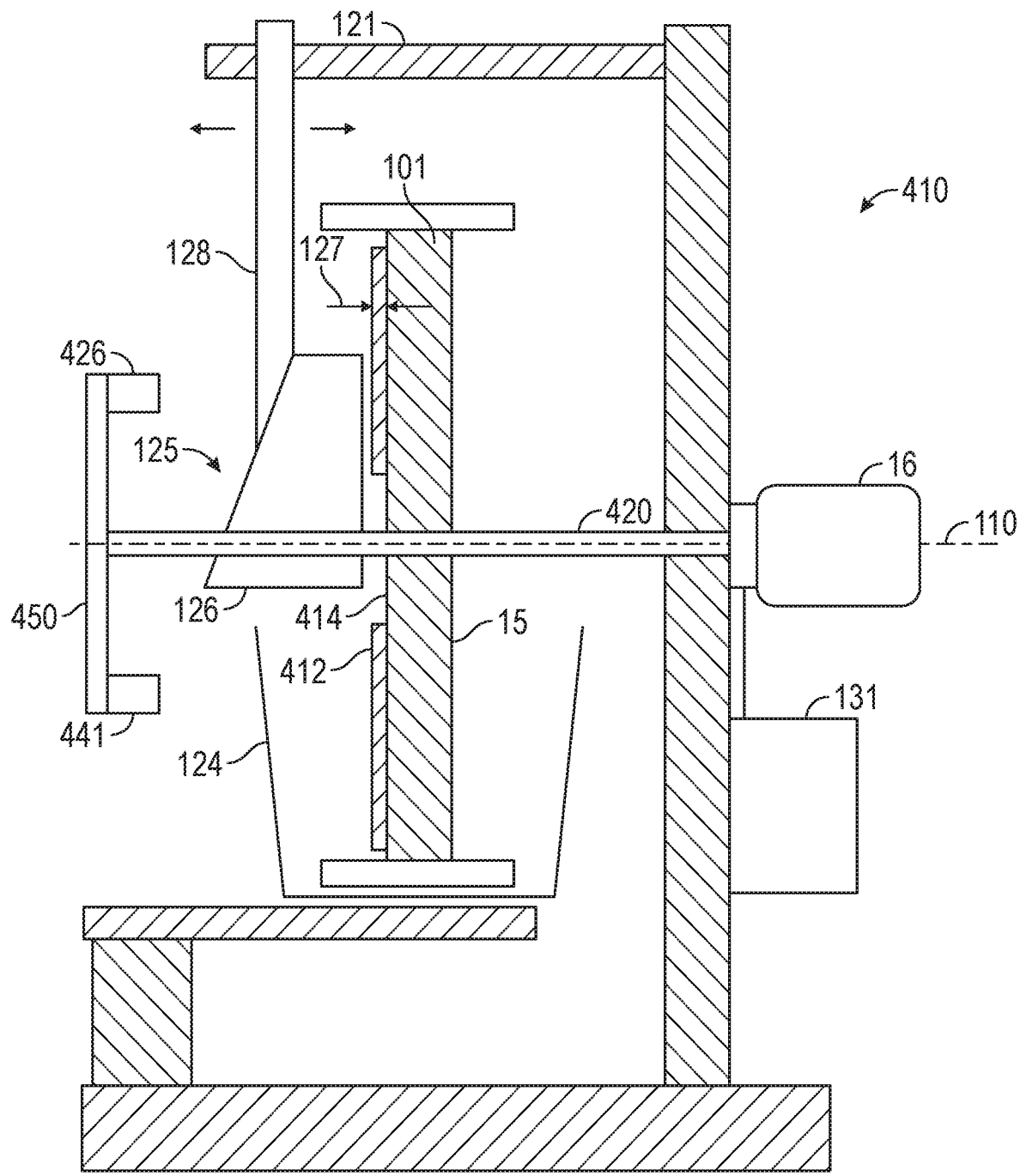
FIG. 4 is a cross-sectional side view of an apparatus for measuring spatial properties of a moving surface coating in accordance with another embodiment.

In another embodiment and as shown in FIG. 4, the light detection device 426 can be arranged to detect characteristics of the surface coating 412 while having movement synchronized with the moving surface 414. In this embodiment, an apparatus 410 similar to that shown in FIGS. 1-3 may be employed, but with the light detection device 426 affixed to rotate in conjunction with the rotatable disk 101 such that the light detection device 426 and the rotatable disk 101 move in concert without relative movement therebetween. For example, the light detection device 426 may be affixed to the shaft 420 through a mounting arm 450, with a counter balance or a second light detection device 441 affixed to the shaft 420 opposite the light detection device 426 to provide for balanced rotation. With this embodiment, high quality still images of the surface coating 412 may be captured while the surface coating 412 is in motion without requiring a high speed camera. The light detection device 426 may also be synchronized with the lighting source (not shown), with the light source static relative to the rotatable disk 101, to capture images every time the light detection device passes the preselected interrogation zone (not shown) when the light source is providing illumination. In embodiments, the light detection device 426 may also be configured to capture continuous video images of the moving surface coating 412.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

What is claimed is:

1. An apparatus for measurement of spatial properties of a moving surface coating containing flake pigment, wherein the apparatus comprises:
   a movable surface adapted to receive the surface coating;
   a motion device in mechanical communication with the movable surface for moving the movable surface;
   a light source positioned to provide a beam of light directed at a preselected interrogation zone through which at least a portion of the movable surface passes during movement thereof;
   a light detection device positioned to detect light reflected from the preselected interrogation zone through which at least the portion of the movable surface passes during movement thereof, wherein the light detection device produces an output comprising data representative of a detected intensity of scattered light and area of scattered light reflected by individual flake pigments in portions of the surface coating within the preselected interrogation zone;
   a computing device coupled to the light detection device, optionally the light source, and optionally the motion device, wherein the computing device is configured to determine one or more spatial properties of the surface coating based upon the output from the light detection device;
   wherein one or more of the light source, the light detection device, or the computing device are configured to adjust for the movement of the surface coating through the preselected interrogation zone as a variable affecting measurement of reflected light from the preselected interrogation zone by the light detection device.

2. The apparatus of claim 1, wherein the movable surface is a rotatable disk of a thin film device.

3. The apparatus of claim 1, wherein the light detection device comprises a photo diode configured to detect light reflected from the preselected interrogation zone, wherein the photo diode is further configured to convert the detected light into an electrical current.

4. The apparatus of claim 3, wherein the computing device is configured to apply a correlation between duration of reflected light detected from the photo diode and a dimension of a flake pigment that provides the reflected light at a preset movement speed of the movable surface to thereby adjust for movement of the surface coating through the preselected interrogation zone as a variable affecting detection of reflected light.

5. The apparatus of claim 3, wherein the computing device is configured to determine sparkle of the surface coating based upon frequency, intensity, and duration of reflected light from the flake pigments as detected by the photo diode.

6. The apparatus of claim 1, wherein the light detection device is an imaging device having a preset sensitivity, and wherein the output produced by the light detection device is an optical image.

7. The apparatus of claim 6, wherein the light source and, optionally, the computing device are configured to provide selective modulation of light from the light source at a predetermined illumination duration based on movement speed of the surface coating and, optionally, size of the flake pigments and at an intensity based on the preset sensitivity of the imaging device with modulation conducted.

8. The apparatus of claim 7, wherein the computing device is configured to determine sparkle of the surface coating by integrating intensity and intensity area in the optical image for at least one range of intensities and at at least one angle of illumination.

9. The apparatus of claim 7, wherein the computing device is configured to determine coarseness of the surface coating based on particle dimensions in the optical image.

10. A method of measuring spatial properties of a moving surface coating containing flake pigment, wherein the method comprises the steps of:
    moving a movable surface having the surface coating disposed thereon;
    directing a beam of light at a preselected interrogation zone through which at least a portion of the movable surface passes during movement thereof;
    detecting light reflected from the preselected interrogation zone through which at least the portion of the movable surface passes during movement thereof using a light detection device to produce an output comprising data representative of a detected intensity of reflected light and area of reflected light from individual flake pigments in portions of the surface coating within the preselected interrogation zone;
    determining one or more spatial properties of the surface coating based upon the output from the light detection device using a computing device;
    wherein the movement of the surface coating through the preselected interrogation zone is adjusted as a variable affecting detection of reflected light from the preselected interrogation zone by the light detection device.

11. The method of claim 10, wherein moving the movable surface comprises rotating the movable surface about an axis.

12. The method of claim 10, wherein detecting light reflected from the preselected interrogation zone comprises detecting light reflected from the preselected interrogation zone with a wet surface coating within the preselected interrogation zone.

13. The method of claim 10, wherein detecting light reflected from the preselected interrogation zone comprises producing an optical image as the output using an imaging device having a preset sensitivity.

14. The method of claim 13, wherein detecting light reflected from the preselected interrogation zone comprises producing an electrical current as the output.

15. The method of claim 14, wherein determining one or more spatial properties of the surface coating using the computing device comprises applying a correlation between duration of reflected light that produces the electrical current and a dimension of a flake pigment that provides the reflected light at a preset movement speed of the movable surface to thereby adjust for movement of the surface coating through the preselected interrogation zone as a variable affecting detection of reflected light.

16. The method of claim 13, wherein directing the beam of light comprises modulating the beam of light at a predetermined illumination duration based upon movement speed of the surface coating and, optionally, size of the flake pigments and at an intensity based on the preset sensitivity of the imaging device.

17. The method of claim 16, wherein modulating the beam of light at the predetermined illumination duration comprises modulating the beam of light to provide illumination for periods of from about 5 ns to about 5 µs.

18. The method of claim 16, wherein determining the one or more spatial properties comprises determining sparkle of the surface coating by integrating intensity and intensity area in the optical image for at least one range of intensities and at at least one angle of illumination.

19. The method of claim 16, wherein determining the one or more spatial properties comprises determining coarseness of the surface coating based on particle dimensions in the optical image.

20. A method of measuring spatial properties of a moving surface coating containing flake pigment, wherein the method comprises the steps of:
- providing a wet surface coating on a substrate, wherein the wet surface coating is adapted to move through a preselected interrogation zone;
- directing a beam of light at the preselected interrogation zone through which at least a portion of the wet surface coating passes during movement thereof;
- detecting light reflected from the preselected interrogation zone through which at least the portion of the wet surface coating passes during movement thereof using a light detection device to produce an output comprising data representative of a detected intensity of reflected light and area of reflected light from individual flake pigments in portions of the surface coating within the preselected interrogation zone;
- determining one or more spatial properties of the wet surface coating based upon the output from the light detection device using a computing device;
- wherein the movement of the wet surface coating through the preselected interrogation zone is adjusted as a variable affecting detection of reflected light from the preselected interrogation zone by the light detection device.

\* \* \* \* \*